United States Patent [19]
Kemp et al.

[11] Patent Number: 6,096,350
[45] Date of Patent: Aug. 1, 2000

[54] COMPOSITIONS AND METHODS FOR PREVENTION AND TREATMENT OF DISEASES ASSOCIATED WITH HONEY BEES

[75] Inventors: G. Kere Kemp, Mercer Island, Wash.; Robert D. Kross, Bellmore, N.Y.

[73] Assignee: Alcide Corporation, Redmond, Wash.

[21] Appl. No.: 08/525,481

[22] Filed: Sep. 8, 1995

[51] Int. Cl.⁷ ................................................ A01N 59/08
[52] U.S. Cl. .......................... 424/661; 424/665; 449/1; 449/2; 449/3; 449/5; 449/17
[58] Field of Search ................................ 424/661, 665; 449/1, 2, 3, 5, 17

[56] References Cited

U.S. PATENT DOCUMENTS

| | | | |
|---|---|---|---|
| Re. 31,779 | 12/1984 | Alliger | 252/187.23 |
| 3,585,147 | 6/1971 | Gordon | 252/187 |
| 3,591,515 | 7/1971 | Lovely | 252/187 |
| 3,954,969 | 5/1976 | Reinert et al. | 424/93 |
| 4,330,531 | 5/1982 | Alliger | 424/149 |
| 4,891,216 | 1/1990 | Kross et al. | 424/78 |
| 4,956,184 | 9/1990 | Kross | 424/661 |
| 4,986,990 | 1/1991 | Davidson et al. | 424/665 |
| 5,100,652 | 3/1992 | Kross et al. | 424/53 |
| 5,185,161 | 2/1993 | Davidson et al. | 424/665 |
| 5,384,134 | 1/1995 | Kross et al. | 424/661 |
| 5,389,390 | 2/1995 | Kross | 426/332 |
| 5,597,561 | 1/1997 | Kross | 424/78 |
| 5,651,977 | 7/1997 | Kross | 424/419 |

FOREIGN PATENT DOCUMENTS

| | | |
|---|---|---|
| 287 074 A2 | 10/1988 | European Pat. Off. . |
| 3308017 C1 | 3/1984 | Germany . |
| 4215534 C1 | 6/1993 | Germany . |
| 1-289429 | 11/1989 | Japan . |
| WO 85/04107 | 9/1985 | WIPO . |
| WO 89/03179 | 4/1989 | WIPO . |

OTHER PUBLICATIONS

U.S. Ser. No. 08/052,641, Davidson et al., filed Apr. 23, 1993.

Lackett et al., "Oxodene: Longevity of Honey Bees" *Journal of Economic Entomology* 65(1): 19–20, 1972.

Shimanuki et al., "Fumigation with ethylene oxide to control disease of honey bees," *Chemical Abstracts* 85: 150, Abstract No. 88387, 1976.

*Primary Examiner*—Peter O'Sullivan
*Attorney, Agent, or Firm*—Seed and Berry LLP

[57] ABSTRACT

Compositions and methods for disinfecting bee colonies for preventing or treating diseases in honey bees, honey bee larvae and honey bee hives are disclosed. Such diseases may arise from a variety of sources, including bacteria, fungi, viruses, protozoa and parasites in the hive. Representative diseases preventable or treatable by this invention include Foulbrood and Chalkbrood. The compositions of the present invention include a protic acid and a chlorite ion, and may further include other optional components such as a gelling agent, colorant and/or preservative. Methods disclosed herein include applying the composition to a surface of a bee-hive. Honey produced by bees administered a composition of this invention is also disclosed.

34 Claims, 1 Drawing Sheet

COMPOSITIONS AND METHODS FOR PREVENTION AND TREATMENT OF DISEASES ASSOCIATED WITH HONEY BEES

TECHNICAL FIELD

The present invention relates generally to the prevention and/or treatment of diseases in honey bees, honey bee larvae and honey bee hives, and more specifically, to compositions and methods useful for treating Chalkbrood and Foulbrood.

BACKGROUND OF THE INVENTION

The honey bees in America and in Europe are various races of *Apis mellifera*. Other related species worldwide used for honey production include *Apis cerana, Apis dorsata* and *Apis florea*. There are numerous diseases threatening honey bee families, and thus their honey production. These diseases arise from many sources, including bacteria, fungi, protozoa and mites. The ones responsible for the greatest economic losses are: Foulbrood-American and European (bacteria), Chalkbrood (fungus), Nosema (protozoan), and Varroa (mite).

American Foulbrood, which is found on every continent, is caused by the spores of the bacterium *Bacillus larvae*, which can remain viable indefinitely on beekeeping equipment. It infects the gut of worker, drone and queen larvae and, while it may not destroy a colony in the first year, if left unchecked may ultimately lead to the death of the colony. The main method of treatment is with the antibiotic oxytetracycline, administered in various forms with a sugar carrier. However, there are many problems associated with administration of oxytetracycline, including problems related to stability, antibiotic contamination of the honey, the possibility of killing open brood on the face of brood combs, and unevenness of dosing. European Foulbrood disease is caused by the bacterium *Melissococcus pluton*, which is fed to the worker, drone and queen larvae by nurse bees. Diseased colonies fail to increase normally so that no surplus honey, in excess of that needed by the colony to survive, is available for the beekeeper. Oxytetracycline is also used for treating such diseased colonies, but the most efficient dosing system for treating American Foulbrood, using Extender Patties, does not work well for this disease.

Chalkbrood disease is caused by the fungus *Ascosphaera apis*, which primarily infects larvae of workers and drones. Infected larvae become overgrown with a white cotton-like mycelium and eventually dry to a hard, white or gray shrunken mass (thus the name Chalkbrood) referred to as a mummy. The fruit-bodies of the fungus develop on the gray-colored mummies, and the spores released from the spore capsules can enter the air of the beehive. This prompts repeated infection of the developing brood through feeding by the cleaning bees. As a result of infection, the colonies fail to grow to a sufficiently large size, their resistance becomes impaired and their honey-producing capacity decreases to a degree depending on the severity of the mycotic infection. The disease is prevalent in the entire temperate zone, spreading apparently from southeastern Europe westward. Massive outbreaks have occurred since 1990 in Hungary, where infection rates of 90–100% are common in certain apiaries. There, the infected bee colonies were not able to produce enough honey, and on many occasions beekeepers found empty hives. No chemotherapeutic agent is available for the control of this disease. Chlorine gas has been investigated, but it fails to kill the spores. The most promising approach to control Chalkbrood is to maintain populous colonies to make up for losses in honey, as well as to use stocks that show evidence of resistance to the organism. A related infection, Stonebrood disease (forming stone-hard larvae) is caused by the fungus Aspergillus flavus and related species. These are common organisms, and difficult to eliminate.

While the above bacterial and fungal diseases affect the larvae of honey bees, the protozoan Nosema disease, caused by the microsporidian Nosema apis Zander, is by far the most widespread of the adult honey bee diseases. The symptoms of Nosema disease are often confused with other causes, and infect individual honey bee workers in many ways. The life span of infected bees is reduced, and can fall to 22%–44% of normal. Also the infected nurse bees are less able to feed brood. Honey bee death rates exceed birth rates, leading to reduced nectar collection and depressed honey yields. Fumigation of empty hives with ethylene oxide and acetic acid has been used to reduce contamination, as has thermal sterilization of hive equipment. The only chemotherapeutic agent that has shown some success, of the many tested, is fumagillin, administered in a sugar syrup.

Bees are attacked by a number of viruses, causing such conditions as Sacbrood Disease and paralysis. These viral diseases are generally not treated, but also do not pose a significant economic threat.

The parasitic honey bee mites *Acarapis woodi* (Acariosis) and *Varroa jacobsoni* (Varroasis), which are found on every continent except Australia, also affect adult honey bees. The mites are difficult to detect, and their discovery in 1921 and the concern over the potential impact on beekeeping in the United States led to enactment of the Honeybee Act of 1922, which restricted the importation of honey bees from countries where the mites were known to exist. When over 30% of the bees in a colony becomes parasitized with mites, honey production is reduced, as is the likelihood of winter survival.

The deficiency of reliable treatments for many of these diseases, affecting both bee larvae and adults is a major problem. A significant improvement in the survival of bee larvae and the extension of the life span of adult bees would be of great value to the beekeeping industry, allowing more bees to make more trips to gather nectar, pollen, water and propolis, thus ensuring greater honey production.

Accordingly, there is a need in the art for improved compositions and methods for controlling and treating infections in honey bees, such as Foulbrood and Chalkbrood Diseases. The present invention fulfills these needs and provides further related advantages.

SUMMARY OF THE INVENTION

In brief, this invention is directed to compositions and methods useful for preventing and/or treating diseases associated with honey bees, honey bee larvae and/or honey bee hives. Such diseases may arise from a variety of sources, including bacteria, fungi, viruses, protozoa and parasites. Representative diseases which are preventable or treatable by the compositions and methods of this invention include Foulbrood and Chalkbrood. In one aspect, the present invention provides methods for treating infected honey bee hives, comprising applying to the hive an effective amount of an aqueous composition comprising a protic acid and a chlorite ion. Optionally, the composition may further contain a gelling agent, a preservative and/or a colorant.

In a preferred embodiment, the method further comprises the step of mixing a first phase and a second phase prior to applying the composition, wherein the first phase comprises the protic acid and the second phase comprises the chlorite ion.

In a related aspect, the composition is applied by spraying or by deposition to the top and/or bottomboards of the hive drawer, or to a flat (e.g., metal) surface introduced over the top and bottomboards, or into a tray or container (e.g., plastic or metal) placed on the top of the bottomboards. In a further embodiment, the composition is in the form of a gel which elicits, upon drying, a strong cleaning instinct in the honey bees, causing the honey bees to transport the dried composition to a location outside of the hive. In still a further embodiment, the protic acid, such as formic acid or acetic acid, is effective as a hive fumigant.

In yet a further aspect, this invention is directed to honey produced by a honey bee colony, wherein the honey bees, honey bee larvae and/or honey bee hives have been administered a composition of this invention for the prevention or treatment of a disease associated with the honey bees, honey bee larvae and/or honey bee hives. In a related embodiment, honey bee colonies are disclosed having been treated with a composition of the present invention.

These and other aspects of the present invention will become apparent upon reference to the detailed description that follows.

DETAILED DESCRIPTION OF THE INVENTION

Figure 1:
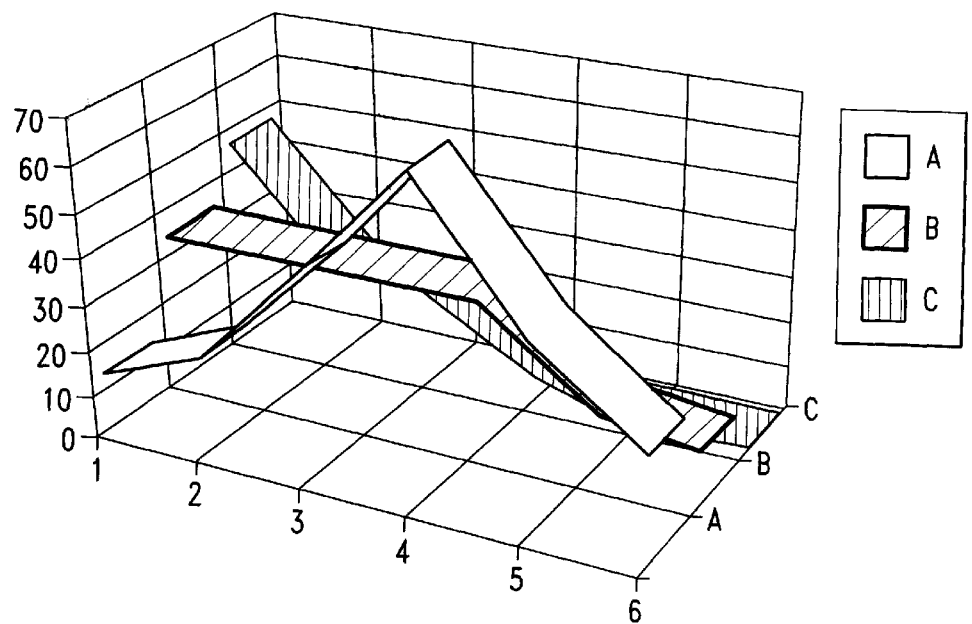
FIG. 1 illustrates the total number of mummies (gray and white) for Chalkbrood-infected hives following treatment with a representative composition of this invention.

As noted above, the present invention is generally directed to compositions and methods for the prevention and/or treatment of diseases in honey bees, honey bee larvae and/or honey bee hives arising from various bacterial, fungal, viral, protozoal and parasitic sources. Such sources cause a variety of diseases, including Foulbrood (American and European), Chalkbrood, Nosema, Acariosis, Varroasis and Sacbrood disease. These diseases can afflict either the larval stage or the adult stage of the honey bee.

The compositions of this invention are aqueous solutions comprising a protic acid and a chlorite ion. Optionally the compositions may further comprise a gelling agent to facilitate the deposition of greater quantities of the composition onto hive surfaces, a colorant to facilitate visualization of the applied composition by the user and/or the bee, and a preservative (for the protic acid).

In the context of the present invention, the term "protic acid" refers to any acid or mixture of acids (including organic acids and inorganic acids) capable of providing an ionizable hydrogen ion (i.e., a "proton"), and thereby reducing the pH of the composition to below about 6. Representative organic acids include, but are not limited to, acids of the general formula:

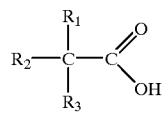

wherein $R_1$ and $R_2$ are independently selected from —H, —$CH_3$, —$CH_2$, COOH, —$CH_2OH$, —$CH_2(OH)COOH$ and —$C_6H_5$; and $R_3$ is either —H or —OH. In the embodiment when $R_3$ is an —OH, the protic acid is an α-hydroxy organic acid having a pK ranging from about 2.8 to about 4.2, and more preferably from about 3.0 to about 4.0. Typical α-hydroxy organic acids include citric, malic, tartaric glycolic, mandelic and lactic acid, as well as mixtures thereof In the embodiment when $R_3$ is —H, the boiling point of the acid (at 760 mm Hg atmospheric pressure) is typically between 100° C. and 120° C., and has a pK ranging from about 4.0 to about 5.0. Typical organic acids in this category are formic and acetic acids. With regard to inorganic acids, such acids include (but are not limited to) acids having a pK ranging from about 0 to about 2.2, such as sulfuric, hydrochloric, nitric and phosphoric acid.

Those of ordinary skill in the art will recognize that the concentration of protic acid in the composition will vary, depending inter alia upon the strength of the protic acid and, in some cases, its volatility. Organic acids will generally be present in an amount ranging from about 0.05% to about 10%, preferably from about 0.1% to about 2% for α-hydroxy acids and from 0.1% to about 5% for volatile, non-α-hydroxy acids. Stronger inorganic acids will generally be present in an amount from about 0.005% to about 0.5% by weight of the composition. In either case, the amount of protic acid in the composition is sufficient to lower the pH of the composition to below about 6, preferably from about 2 to about 5, and more preferably from about 2.5 to about 4.5.

The chlorite ion component is preferably produced by aqueous dissociation of a water soluble chlorite, such as a metal chlorite. The term "metal chlorite" encompasses both alkali metal chlorites and alkaline earth metal chlorites, including the so-called "stabilized chlorine dioxide" products that contain a metal chlorite. Sodium chlorite and potassium chlorite are preferred, with sodium chlorite being particularly preferred. The chlorite ion is typically present in the composition in an amount ranging from about 0.01% to about 1.0% by weight. Preferably, the chlorite is present in an amount ranging from about 0.05% to about 0.75%, and more preferably from about 0.1% to about 0.65% by weight of the composition.

In the practice of this invention, the proton from the protic acid and the chlorite ion partially react to generate chlorous acid. The chlorous acid that is formed, in equilibrium with chlorite ion, then degrades via a series of cidal intermediates, ultimately forming the cidal species chlorine dioxide if the reaction is not short-circuited by reaction with other oxidizable organic matter in the environment. The anti-microbial, anti-fungal, anti-viral, anti-protozoal and anti-mital activity of the composition is achieved by action of the water-soluble cidal species on the contacted surfaces, as well as the action of any gaseous chlorine dioxide formed, which can additionally transport to other hive surfaces. The gaseous cidal action can be augmented by that of the vapors of the volatile acid, such as acetic or formic acid, when such is used to acidify the chlorite.

Inasmuch as the level of oxidative cidal agents within the acid/chlorite combination decreases with time, the composition may be formulated as a two phase product to allow combination of the protic acid and chlorite ion immediately prior to use (i.e., preferably within 4 hours, and more preferably within 1 hour of application for most formulations). The protic acid phase and the chlorite ion phase may be combined, prior to application, in suitable ratios to achieve the above concentrations. Preferably, the two phases are formulated in aqueous solvents such that the solutions are combined in approximately equal parts by volume prior to use. Alternatively, one or both parts can be provided in solid powder or granular forms, which can be added to water separately and/or sequentially with stirring, in order to produce the final composition.

Optionally, the composition additionally comprises one or more of the following: a gelling agent, a preservative and/or a colorant. A gelling agent is any compound which, when added to the composition, increases its viscosity. This facilitates the application to, and retention of greater quantities of the composition when applied to hive surfaces. Suitable gelling agents include naturally occurring organic polymers, such as guar and locust-bean gums, synthetic polymers based an cellulose, such as methyl cellulose and hydroxyethyl cellulose, poly(acrylamide) and its derivatives, such as poly(acrylamido methanesulfonic acid), and inorganic gellants, such as the Veegums, mixtures of aluminum and magnesium silicates, which impart thixotropic properties to the compositions thereby facilitating their application. Particularly preferred are gelling agents which create compositions that elicit a strong cleaning instinct in the bee, prompting it to remove residues of the composition from the hive and, in so doing, contacting its body with the material. This contact serves to reduce or eliminate the disease from the bee's body. Gelling agents in this category include poly(acrylamido methanesulfonic acid) and the Veegums. The amount of gelling agent in the composition will depend upon the nature and size of the gelling agent molecule, but generally ranges from about 0.1% to about 5%, and typically 0.3% to about 3% by weight of the composition.

The optional preservative, which is typically included in the protic acid phase, comprises any suitable preservative known in the art to be stable and functional in acid environments. This includes (but is not limited to) benzoic acid, sorbic acid, propionic acid and the methyl ester of p-hydroxybenzoic acid. Such preservatives may comprise up to about 0.2%, typically from about 0.02% to about 0.1%, and preferably from about 0.02% to about 0.08% by weight of the protic acid phase.

The optional colorant may be any suitable water-soluble dye known in the art to be stable in the appropriate acid or chlorite phase, including (but not limited to) FD&C Yellow No. 5, FD&C Blue No. 1 and methylene blue. Such dyes, which may slowly fade in the mixed composition, comprise up to about 0.2%, and typically from about 0.005% to about 0.15% by weight of the composition.

The compositions of this invention may be applied to a surface of the bee-hive by any appropriate means known to those skilled in the art. A preferred application is by spraying, using a spray bottle or a pump. In this practice of the application, when a gelled formulation is being applied, the use of a relatively wide aperture may be beneficial. In another preferred application of this invention, the mixed composition is applied, by brush, to a sheet of rigid plastic or metal foil of such dimensions as to fit the hive bottom (or top). Once applied, the sheet is slipped under the frame of the bee-hive, with the treated surface inward. For infected, populated hives, the treatment may be repeated at one-week intervals until the disease is eliminated. In the case of very severe infection, the treatment should be repeated every 3–4 days. An indication of a very severe infection, with Chalkbrood disease, is if the number of fallen mummies exceeds 50 per week.

An additional preferred application is the introduction of a volume of liquid or gel composition to a tray reservoir, for insertion into the bottom of a hive. A sufficient volume is selected so as to maintain a liquid reservoir in the tray, despite its evaporative losses, in order to provide action over a 2–4 week period. The reservoir of liquid acts to disinfect fallen mummies, preventing their further contamination of the hive, and also as a continuing source of the cidal gaseous vapors from the volatile acid used to acidify the chlorite.

When bee-hives are first opened in the spring, it is advisable to spread the composition directly onto the hive bottom. For prophylactic use, the inside of empty bee-hives should be treated, preferably by spraying, 3 days before stocking with bees. Bee-hive accessories used in other hives (feeders, partition planks, queen excluders, blind frames, screening mesh) should be disinfected by treating their entire surfaces with the composition 2–3 days before placing them back in the hive.

In general, with populated hives, the composition should not be applied in the mornings, to avoid heat-induced rapid decomposition associated with higher temperatures, and the resulting rapid generation of chlorine dioxide which may adversely affect the bee population. Hives exposed to direct sunlight should be treated in late afternoon hours. Conversely, where there is a need for enhanced fumigation of hives, primarily empty hives, applications should be made in warmer temperatures, where the use of acetic or formic acid as the protic acid contributes to the activity. The latter is particularly advantageous in eliminating Chalkbrood fungal spores and mites.

The present invention is illustrated by the following examples, which are to be regarded as illustrative rather than restrictive. Unless otherwise noted, all parts and percentages in the examples, as well as the specifications and claims, are by weight.

EXAMPLES

Example 1

Gelled Composition for Treating a Populated Bee-hive

This example illustrates the preparation of a representative composition of this invention for controlling Chalkbrood disease in a populated bee-hive.

A chlorite ion phase was prepared by mixing the following ingredients:

| Component | Level (%) |
| --- | --- |
| Sodium chlorite | 0.64 |
| Triton X-100 | 0.45 |
| Poly(acrylamido methanesulfonic acid) 16% aqueous solution | 15.00 |
| Tetrasodium EDTA | 0.19 |
| Sodium hydroxide (1N) solution | 20.00 |
| Titanium dioxide | 0.01 |
| Water, purified | q.s. |

A protic acid phase was prepared by mixing the following ingredients:

| Component | Level (%) |
| --- | --- |
| Lactic acid | 2.64 |
| Natrosol 250 MR | 1.00 |
| Pluronic F-68 | 0.40 |
| Isopropyl alcohol | 2.00 |
| FD&C No. 5 | 0.30 |
| Sodium benzoate | 0.04 |
| Water, purified | q.s. |

The two phases were blended together in approximately equal volume amounts, just prior to application, and painted onto aluminum foil sheets which were then slid, treated side upwards, into the bottoms of populated bee-hives. The sheets were recoated weekly with the composition.

Example 2
Spray Composition for Disinfecting a Bee-hive

This example illustrates the preparation of a representative composition for disinfecting populated bee-hives and for spraying empty hives and hive equipment.

A chlorite ion phase (concentrate) was prepared by mixing the following ingredients:

| Component | Level (%) |
| --- | --- |
| Sodium chlorite | 3.03 |
| Poloxamer 188 | 3.00 |
| Tetrasodium EDTA | 0.53 |
| Sodium hydroxide (1N) solution | 20.00 |
| Water, purified | q.s. |

A protic acid phase (concentrate) was prepared by mixing the following ingredients:

| Component | Level (%) |
| --- | --- |
| Lactic acid | 16.72 |
| Water, purified | q.s. |

The two phases were individually stirred into tap water, in a mix volume ratio of 1 part of each concentrate to 16 parts of tap water. The solution was sprayed onto the bottomboards of populated bee-hives infected with Chalkbrood disease and the boards then slid, sprayed side upwards, into the hive bottom. Approximately ½-liter of solution was used for each hive.

Example 3
Composition for Disinfecting and Fumigating a Bee-hive

This example illustrates the preparation of a representative composition for disinfecting populated bee-hives and for fumigating empty hives.

A chlorite ion phase (concentrate) is prepared as in Example 2. A protic acid phase (concentrate) is prepared as in Example 2, except that formic acid is used in place of lactic acid at the same level of inclusion. The two phases are individually stirred into tap water, in a mix volume ratio of 1 part of each concentrate to 16 parts of tap water. The solution is painted onto the bottomboards of empty bee-hives infected with Foulbrood or other disease-causing bacteria, pathogenic protozoa or mites, and the boards then slid, sprayed side upwards, into the hive bottom. Approximately ½-liter of solution is used for each hive. The treatment is repeated every 3 days, for 5 applications.

Example 4
Composition for Disinfecting a Populated Bee-hive

This example illustrates the preparation of a representative composition for disinfecting populated bee-hives.

A chlorite ion phase is prepared by mixing the following ingredients:

| Component | Level (%) |
| --- | --- |
| Sodium chlorite | 0.50 |
| Water, purified | q.s. |

A protic acid phase is prepared by mixing the following ingredients:

| Component | Level (%) |
| --- | --- |
| Mandelic acid | 2.35 |
| Acetic acid (glacial) | 3.69 |
| Water, purified | q.s. |

The two phases are blended together in approximately equal volume amounts, just prior to application, and painted onto rigid plastic sheets which are then slid, treated side upwards, into the bottoms of populated bee-hives which are infested with tracheal mites. The sheets are recoated every 2–3 days with the composition. The volatile chlorine dioxide, which forms as a partial degradation product of the acidified chlorite, combines with the acetic acid vapors to treat the bees and disinfect those portions of the hive where only airborne disinfectants can permeate.

Example 5
Treatment of Chalkbrood Disease with a Gelled Composition

This example illustrates the use of the representative gelled composition of Example 1 for the control of Chalkbrood disease. The trial was carried out over a one-year duration, in nine hives each of two hive types, all of which were infected with the Chalkbrood fungus. Rigid aluminum foil sheets were cut to a size identical with the internal measurements of the hives, and two sheets per hive were coated on one side, by brushing on a 1:1 volume mix of the indicated composition. On the average, 11.6 gms of the composition were applied per sheet. One foil was placed in the upper part of the infected, populated hive, with its treated side down. The other foil was placed on the bottom plank of the hive, with its treated side up. The upper sheet was cut so that it did not cover the entire frame surface, but left a few centimeters uncovered in front. A first set of sheets was applied in mid-July, a second replacement set was inserted three weeks later (early August). The second replacement set was removed from the hives in the autumn, when winter clustering began. Observations of hive health were taken (a) the day before the first set of sheets were inserted, (b) the replacement date of the first set of sheets with the second set of sheets, and (c) one year after the first set of sheets were inserted.

The small level of chlorine dioxide released from the foils in the hives were observed to have elicited a pronounced cleaning response from the bees, which also carried out the calcified, infected pupae. It was further noted that, when the sheets were withdrawn at both times, all the yellow residues of the dried composition had been removed by the bees. This continual removal of calcified mummies is recommended by bee-keepers as a means of controlling the proliferation of the Ascosphaera fungus.

The above treatments were found to have successfully controlled the calcification of the brood. The one year observation of colonies indicated that the hives were practically healthy, and no mortality was observed in any of the hives treated with the composition. The results of this study are presented in Table 1.

TABLE 1

APPEARANCE OF CALCIFICATION AT THE TIME OF OBSERVATION

| HIVE TYPE | COLONY NO. | (a) Re-Treatment | (b) Replacement | (c) One Year |
|---|---|---|---|---|
| NB Movable Frame | 1 | severely calcified* | non-calcified | clear |
| " | 2 | severely calcified | non-calcified | 1 calcified cell |
| " | 3 | severely calcified | non-calcified | clear |
| " | 4 | severely calcified | non-calcified | clear |
| " | 5 | severely calcified | non-calcified | clear |
| " | 6 | severely calcified | non-calcified | 1 calcified cell |
| " | 8 | severely calcified | 7 calcified cells | clear |
| " | 9 | severely calcified | non-calcified | clear |
| " | 10 | severely calcified | non-calcified | clear |
| HUNOR | 1 | severely calcified | non-calcified | clear |
| " | 3 | severely calcified | non-calcified | clear |
| " | 4 | severely calcified | non-calcified | clear |
| " | 5 | severely calcified | non-calcified | clear |
| " | 6 | severely calcified | non-calcified | clear |
| " | 7 | severely calcified | non-calcified | clear |
| " | 8 | severely calcified | non-calcified | clear |
| " | 9 | severely calcified | non-calcified | 4 calcified cells |
| " | 10 | severely calcified | non-calcified | clear |

(Severely calcified*: 2–3 frames contain laminated calcified brood)

Example 6
Treatment of Chalkbrood Disease with a Gelled Composition

This example illustrates the use of the representative gelled composition of Example 1 for reducing Chalkbrood infestation of severely infected bee-hive colonies. The duration of the studies was approximately 1 month each in the period March—May for two successive years, and the results were compared with untreated, infected hives from the Spring and Summer months of the year prior to the studies. Equal volumes of the composition of Example 1 were mixed in a widemouth plastic dish, and then applied to plastic sheets which conformed in size to the bottoms of the hive. Approximately 8.3 gms of the composition were applied to the upper side of a single sheet, which was then slid into the bottom of each hive. In two successive years, the composition was used to treat 241 and 306 cases, respectively, of Chalkbrood disease. The sheets were replaced at one-week intervals, except in cases where the number of fallen mummies exceeded 50 per week, when changes were made every 3–4 days. Bee-hive entrances were not closed during the treatments.

In the year prior to treatment, losses caused by the fungus Ascosphaera apis occurred over a 140 day period, from early-April to mid-August in the apiary included in this trial. When the preparation was used in the first year of the trial, the losses were confined to a 32-to-42 day period after their onset, while in the following year of the trial the losses occurred over a 35 day period. The honey production capacity of the bee colonies, which was markedly reduced in the year prior to treatment, was deemed satisfactory in both of the trial years. After severe infection which occurred in the year prior to treatment, the colonies showed a complete freedom from infection of 7% in the first year of the trial, which increased to 23% in the second year of the trial. Prior to the treatment of the hives with the composition of Example 1, they were initially treated for one month with either Fumerra cake (containing an antibiotic) or Nystatin. The Fumerra cake resulted in the very rapid development of calcified brood. In all of the experiments with the composition of Example 1, no mummies were found in the last treatment of each hive. The formulation had no apparent side effects on the bees, and was not found to get into the honey. Owing to the clean-up reaction elicited in the bees, no residues remained in the hives.

Example 7

Treatment of Chalkbrood Disease with a Spray Composition

This example illustrates the use of the representative spray composition of Example 2 for reducing Chalkbrood infections of bee-hives. Two different bee-keepers were involved in the experiments. The 6-treatment course ran from July to September, with the first 5 treatments spaced one week apart. The spray was applied to bottomboards of the hives, as described in Examples 5 and 6, and the rate of usage of the spray composition was 1 liter per 24 hives. The hives were sprayed according to the following groupings:

Group A: Control—no spray; infected mummies left (in 7 hives);

Group B: No spray; infected mummies removed (from 10 hives);

Group C: Spray; infected mummies removed (from 10 hives).

The total number of mummies (gray and white) per hive for each of the above groupings during the course of the study were tabulated and are presented in FIG. 1. In Group A, there was a high mummy number throughout the study, peaking at the time of treatment 3. In Group B, removal of mummies effected a considerable improvement, although mummies were still found at the end of the treatment period. No mummies were found for Group C after the fourth treatment.

Figure 2:
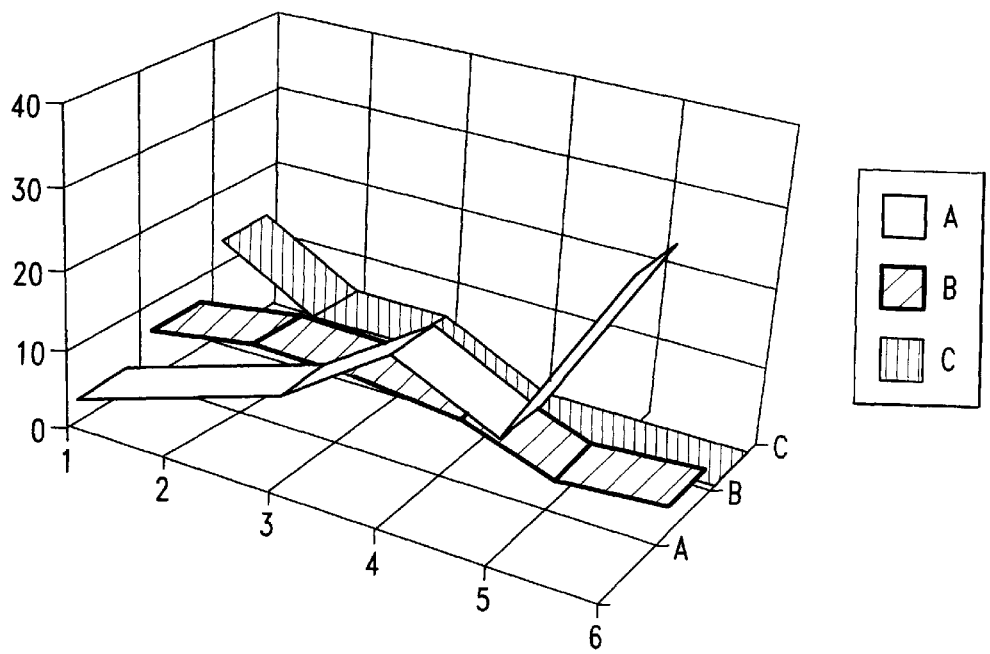
FIG. 2 illustrates the number of gray (infecting) mummies for Chalkbrood-infected hives following treatment with a representative composition of this invention.

The mummies removed in Group B and Group C were separated into gray (infecting) and white. As illustrated in FIG. 2, when the gray (infecting) mummies were tabulated individually, the Group A hives showed a continuous increase, while the trends in Groups B and C were generally the same as total mummy numbers.

The strength of the families in each group were estimated by the numbers of covered honey combs and by the brooding areas. The average number of covered combs per grouping are shown in Table 2 (where the numbers from Group A in July were used for normalization).

TABLE 2

| GROUP | # of families in July | # of families in September | (# July/# Sept.) × 100 |
|---|---|---|---|
| A | 10.9 | 9.7 | 88.9 |
| B | 12.8 | 11.1 | 86.7 |
| C | 15.2 | 14.3 | 94.1 |
| (Group C/Group A) × 100 | 139.4 | 147.4 | — |

As indicated by the data presented in Table 2, while 88.9% of the number of families in the A Group (no mummy removal) and 86.7% of the number of families in the B Group (infected mummies removed) survived to September, the spray-treated families of the C Group had a 94.1% survival rate. Thus, although the number of families in the C Group was 39.4% greater than the A Group at the start of the study, it rose to 47.4% in September. The increase of brooding area showed a similar trend. Based on the above results, spray treatment with the representative composition of Example 2, when used in conjunction with mummy removal as in Group C, proved highly beneficial.

Alternatively, a reservoir or tray containing a composition of this invention may be placed in the bottom of the hive with a "bee excluder" (e.g., an appropriate mesh material) placed over the top of the reservoir tray. This would effectively isolate the bees from the mummies which fall through the mesh and into the composition. In this manner, reduced infection could be achieved without the need for immediate mummy removal from the hive.

From the foregoing, it will be appreciated that, although specific embodiments of this invention have been described herein for the purpose of illustration, various modifications may be made without departing from the spirit and scope of the invention. Accordingly, the invention is not limited except by the appended claims.

What is claimed is:

1. A method for preventing or treating a disease associated with honey bees, honey bee larvae or honey bee hives, wherein the disease arises from a source selected from a bacteria, a fungi, a virus, a protozoa and a parasite, comprising administering to the honey bees, honey bee larvae or honey bee hives an effective amount of an aqueous composition comprising a protic acid and a chlorite ion.

2. The method of claim 1 wherein the disease arises from a bacterial source that causes American Foulbrood or European Foulbrood.

3. The method of claim 1 wherein the disease arises from a fungal source that causes Chalkbrood.

4. The method of claim 1 wherein the disease arises from a protozoan source that causes Nosema.

5. The method of claim 1 wherein the parasitic source is a mite which causes a disease selected from Varroasis and Acariosis.

6. The method of claim 1 wherein the disease arises from a viral source that causes Sacbrood Disease.

7. The method of claim 1 wherein administration is accomplished by applying the composition to a honey bee hive.

8. The method of claim 7 wherein the composition is sprayed on or in the honey bee hive.

9. The method of claim 7 wherein the composition is applied to an internal surface of the honey bee hive.

10. The method of claim 7 wherein the composition is applied to the surface of a substrate inserted into the honey bee hive.

11. The method of claim 10 wherein the substrate is selected from a bottomboard of the hive, a topboard of the hive, and a flat surface introduced over the top or bottomboard of the hive.

12. The method of claim 7 wherein the composition is located in a reservoir internal to the hive.

13. The method of claim 1 wherein the protic acid is an organic acid.

14. The method of claim 13 wherein the organic acid as the structure:

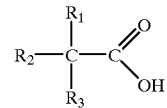

where
$R_1$ and $R_2$ are the same or different, and independently selected from —H, —$CH_3$, —$CH_2COOH$, —$CH_2OH$, —$CH_2(OH)COOH$ and —$C_6H_5$; and
$R_3$ is selected from —OH and —H.

15. The method of claim 14 wherein $R_3$ is —OH, and the pK of the organic acid ranges from about 2.8 to about 4.2.

16. The method of claim 15 wherein the organic acid is selected from citric acid, malic acid, tartaric acid, glycolic acid, mandelic acid, lactic acid, and mixtures thereof.

17. The method of claim 14 wherein $R_3$ is —H, and the pK of the organic acid ranges from about 4.0 to about 5.0.

18. The method of claim 17 wherein the organic acid is selected from formic acid, acetic acid, and mixtures thereof.

19. The method of claim 1 wherein the protic acid is an inorganic acid.

20. The method of claim 19 wherein the inorganic acid as a pK ranging from about 0 to about 2.2.

21. The method of claim 20 wherein the inorganic acid is selected from sulfuric acid, hydrochloric acid, nitric acid, phosphoric acid, and mixtures thereof.

22. The method of claim 1 wherein the protic acid is present in the composition in an amount ranging from about 0.005% to 10% by weight of the composition.

23. The method of claim 15 wherein the organic acid is present in the composition in an amount ranging from 0.1% to 2% by weight of the composition.

24. The method of claim 17 wherein the organic acid is present in the composition in an amount ranging from 0.1% to 5% by weight of the composition.

25. The method of claim 19 wherein the inorganic acid is present in the composition in an amount ranging from 0.005% to 0.5% by weight of the composition.

26. The method of claim 1 wherein the chlorite is a metal chlorite.

27. The method of claim 16 wherein the metal chlorite is sodium chlorite.

28. The method of claim 1 wherein the chlorite ion is present in the composition in an amount ranging from 0.01% to 1.0% by weight of the composition.

29. The method of claim 1 wherein the chlorite ion is present in the composition in an amount ranging from 0.1% to 0.65% by weight of the composition.

30. The method of claim 1 wherein the composition is provided as a two-part composition, wherein the first part comprises the protic acid and the second part comprises the chlorite ion.

31. The method of claim 30 wherein the two-part composition is combined immediately prior to administration.

32. The method of claim 1 wherein the composition further comprises an agent selected from a gelling agent, a preservative and a colorant.

33. The method of claim 1 wherein the composition is in the form of a gel.

34. The method of claim 1 wherein the composition is in the form of a liquid.

* * * * *